United States Patent [19]
Senaratne et al.

[11] Patent Number: 5,654,485
[45] Date of Patent: Aug. 5, 1997

[54] SYNTHESIS OF CYCLOALKYLDIARYLPHOSPHINES

[75] Inventors: K. Pushpananda A. Senaratne; Arcelio J. Malcolm; Felix M. Orihuela; Hassan Y. Elnagar, all of Baton Rouge, La.

[73] Assignee: Albemarle Corporation, Richmond, Va.

[21] Appl. No.: 620,823

[22] Filed: Mar. 25, 1996

[51] Int. Cl.$^6$ .................................................. C07F 9/50
[52] U.S. Cl. .................................................. 568/17
[58] Field of Search .................................................. 568/17

[56] References Cited

U.S. PATENT DOCUMENTS

| | | | |
|---|---|---|---|
| 2,437,795 | 3/1948 | Walling | 568/17 |
| 4,618,720 | 10/1986 | Bay et al. | 568/17 |
| 4,668,823 | 5/1987 | Murray | 568/17 |
| 4,947,000 | 8/1990 | Meguro et al. | 568/17 |
| 5,354,894 | 10/1994 | Devon | 568/17 |
| 5,527,967 | 6/1996 | Millaues | 568/17 |

OTHER PUBLICATIONS

Aguiar et al., "Lithium Diphenylphosphide: A Convenient Source and Some Reactions", JOC Mar. 1962 vol. 27, pp. 1001–1004.

Toth et al., "Aspects of the Cleavage of Phosphines with Potassium: Synthesis and Reactivity of Lithium and Potassium Bis(p–(dimethylamino)phenyl)phosphide", Organometallics 1990, vol. 9, No. 3, pp. 675–680.

Rossi et al., "Reaction of 1–Bromoadamantane with Dipheynlphosphide and Dipheynlarsenide Ions by the SRN1 Mechanism. Facile Nucleophilic Substitution at the Bridgehead Position", J Org Chem 1982, vol. 47, No. 24. pp. 4654–4657.

Aguiar et al., "The Reaction of Lithium Diphenylphosphide and Simple Aryl Halides", Aug. 1963, vol. 28, pp. 2091–2093.

Tsvetkov et al., "A Simple Synthesis and Some Synthetic Applications of Substituted Phosphide and Phosphinite Anions" Synthesis, Mar. 1986, pp. 198–208.

Hayashi et al., "Catalytic Asymmetric Hydroformylation by the Use of Rhodiumcomplexes of Chiral Bidentate Phosphoros Ligands Bearing Saturated Ring Skeletons", Sep. 1979, Bulletin of the Chemical Society of Japan, vol. 52, No. 9, pp. 2605–2608.

Morrison et al., "Synthesis of Menthyl–and Neomenthyldiphenylphosphine. Epimeric, Chrial, Tertiary Phosphine Ligands for Asymmetric Synthesis", J Org Chem, vol. 39, No. 2, 1974, pp. 270–272.

Wittenberg and Gillman, "Lithium Cleavages of Triphenyl Derivatives of Some Group Vb Elements in Tetrahydrofuran", J Org Chem vol. 23, pp. 1063–1065, Jul. 1958.

Kuchen and Buchwald, "Reactions of diphenylphosphine Sodium", Angew Chem 69, pp. 307–308 (1957)—Abstract Attached.

*Primary Examiner*—James H. Reamer
*Attorney, Agent, or Firm*—Philip M. Pippenger

[57] ABSTRACT

By reacting certain partially sterically-hindered chlorosubstituted cycloalkanes with sodium and/or potassium diarylphosphides in an ether reaction medium, not only are useful cycloalkyldiarylphosphines produced, but in addition the chloro-substituted cycloalkane does not undergo any appreciable reaction with the coproduced aryl sodium and/or aryl potassium as it is formed. Moreover, the process makes it possible to avoid or at least to greatly reduce interaction with or cleavage of cyclic ether reaction media such as tetrahydrofuran. Thus the process makes possible improvements both in yield and quality of the cycloalkyldiarylphosphite product. A two-stage process conducted in an ether reaction medium is also described. In the first stage the sodium and/or potassium diarylphosphine reactant is produced by reaction between sodium and/or potassium and triarylphosphine.

26 Claims, No Drawings

SYNTHESIS OF CYCLOALKYLDIARYLPHOSPHINES

TECHNICAL FIELD

This invention relates to an efficacious process for producing cycloalkyldiarylphosphines from triarylphosphines.

BACKGROUND

Cycloalkyldiarylphosphines constitute a group of chemical products of considerable usefulness as ligands for making noble metal catalysts. Menthyldiphenylphosphine and neomenthyldiphenylphosphine are examples of ligands which impart to transition metal complexes the potential for diastereomeric interactions with unsaturated organic substrates, thus making asymmetric synthesis possible. Note in this connection, J. D. Morrison and W. F. Masler, *J. Org. Chem.*, 1974, Vol. 39, No. 2, pages 270–272. Neomenthyldiphenylphosphine is of particular importance for the preparation of noble metal catalysts useful in the synthesis of certain pharmaceuticals such as naproxen, ketoprofen, ibuprofen, etc.

A known method of generating tertiary phosphines with two aryl groups and a dissimilar third hydrocarbyl group involves coupling a lithium diaryl phosphide with a halohydrocarbon such as benzyl chloride in an ether such as tetrahydrofuran. See A. M. Aguiar, J. Beisler and A. Mills, *J. Org. Chem.*, 1962, Vol. 27, pages 1001–1005. Because the reaction co-produces a reactive aryl lithium coproduct which can complicate synthesis procedures, the authors (Aguiar et al.) developed a method of selectively eliminating this coproduct. They accomplished this by adding to the reaction mass an equivalent amount of tert-butyl chloride to selectively react with the aryl lithium so that isobutylene, aromatic hydrocarbon and lithium chloride are formed. Nevertheless an extra reactant and a concurrent reaction were involved in this approach.

Another complicating factor in the reaction of lithium diaryl phosphide with a halohydrocarbon in tetrahydrofuran is that one or more components in the system tend to interact with the tetrahydrofuran whereby side reactions such as ring cleavage can occur under the conditions used. In addition, the reaction between lithium diaryl phosphide and menthyl chloride is slow and requires prolonged reaction periods, which in turn favors the opportunity for more adverse interaction with the cyclic ether solvent such as ring cleavage to occur.

THE INVENTION

It has now been found that by reacting certain partially sterically-hindered chloro-substituted cycloalkanes (cycloalkyl chlorides) with sodium and/or potassium diarylphosphides, not only are useful cycloalkyldiarylphosphines produced, but in addition the chloro-substituted cycloalkane does not undergo any appreciable reaction with the coproduced aryl sodium and/or aryl potassium as it is formed. Moreover, the process of this invention makes it possible to avoid or at least to greatly reduce interaction with or cleavage of cyclic ether reaction media such as tetrahydrofuran. Thus this invention makes possible improvements both in yield and quality of the cycloalkyldiarylphosphite product.

In one of its embodiments this invention provides a process of forming a phosphine of the formula $R^1R^2R^3P$ which process comprises reacting an alkali metal diarylphosphide of the formula $M^{\oplus}\,^{\ominus}PR^1R^2$ with an alkyl-substituted monochlorocycloalkane of the formula $R^3Cl$ in a liquid ether reaction medium in which said phosphide is soluble such that said phosphine is formed, wherein $R^1$ and $R^2$ are the same or different aryl groups, wherein $R^3$ is a mono- or polyalkyl-substituted cycloalkyl group having from 5 to 8 carbon atoms in the ring and where a linear or branched alkyl group of up to about 12 carbon atoms is substituted on one of the ortho positions of the ring, and wherein M is a sodium or potassium atom, or a combination of sodium and potassium atoms. By "soluble" is meant that the reactant is capable of dissolving in the ether reaction medium at the reaction temperature being employed, at least to the extent necessary to enable the reaction to proceed at a reasonable reaction rate. The term does not imply that the reactant must be soluble in all proportions, but in general the greater its solubility in the ether reaction medium, the better.

Other embodiments and features of this invention will be still further apparent from the ensuing description and appended claims.

The alkali metal diarylphosphide used in the process can be represented by the formula $$M^{\oplus}\,^{\ominus}PR^1R^2$$

where $R^1$ and $R^2$ are the same or different aryl groups, which typically contain up to about 24 carbon atoms each, and M is a sodium or potassium atom. The aryl groups may have a single ring or a plurality of rings, and include phenyl, 1-naphthyl, 2-naphthyl, 2-biphenylyl, 3-biphenylyl, 4-biphenylyl, acenaphthyl, phenanthryl, tetrahydronaphthyl, and like aromatic groups. The aryl groups can be substituted or unsubstituted, and when substituted can contain one or more substituents inert to the alkali metals, such as one or more: alkyl groups, alkenyl groups, hydrocarbyloxy groups, hydrocarbylthio groups, hydrocarbylcarbonyl groups, hydrocarbyloxyhydrocarbyl groups, dihydrocarbylamino groups, and heteroaromatic groups, and combinations of two or more of these. Preferably, the aryl groups are phenyl groups each of which is either unsubstituted or has up to 3 alkyl substituents having up to about 4 carbon atoms each. Phosphides in which the two aryl groups are the same are preferred, and most preferred are sodium diphenylphosphide and potassium diphenylphosphide.

The alkyl-substituted monochlorocycloalkane, also known as an alkyl-substituted cycloalkyl chloride, can be represented by the formula $$R^3Cl$$

where $R^3$ is a mono- or polyalkyl-substituted cycloalkyl group preferably having from 5 to 8 carbon atoms in the ring and where a linear or branched alkyl group of up to about 12 carbon atoms is substituted on one of the ortho positions of the ring. In addition to this required ortho-alkyl substitution, the ring may contain other substituents which are innocuous in the sense that they will not impair or inhibit the desired reaction. While such additional substituents can be in any positions which do not unduly sterically hinder the chlorine atom, such substituents are preferably in the meta or para positions relative to the chlorine substitution. Examples of such innocuous substituents include alkyl groups, alkenyl groups, hydrocarbyloxy groups, hydrocarbylthio groups, hydrocarbylcarbonyl groups, hydrocarbyloxyhydrocarbyl groups, and heteroaromatic groups, dihydrocarbylamino groups, and combinations of two or more of these. Typically in the practice of this invention, this reactant will contain a total of up to about 24 carbon atoms, and preferably up to about 18 carbon atoms, in the molecule. As regards ring size, most preferably the ring is a 6-membered ring. The ortho-alkyl substituent is preferably a secondary alkyl group which most preferably contains up to about 6 carbon atoms. A particularly preferred reactant is menthyl chloride.

Any ether reaction medium in which the sodium diarylphosphide and/or potassium diarylphosphide and the alkyl-substituted cycloalkyl monochloride reactants are soluble and that exists in the liquid state under the reaction conditions being used is suitable for use in the conduct of this reaction. The ethers may be monoethers or polyethers, they may be saturated or unsaturated, and they may be cyclic or acyclic, but in any case should be free of any functionality that would interfere with or inhibit the desired reaction. Examples of polyethers include 1,2-dimethoxyethane, diglyme, 1,4-dioxane, tetrahydrofurfuryl ethyl ether, tetrahydrofurfuryl n-butyl ether, and similar polyethers. Preferably, the ether is one or more saturated hydrocarbyl monoethers, or one or more a hydrocarbyl monoethers having at least one aromatic group in the molecule. Examples include dialkyl ethers, dicycloalkylethers, diaryl ethers, monoalkylmonoaryl ethers, monocycloalkylmonoaryl ethers, monoalkylmonocycloalkyl ethers, and saturated cyclic monoethers, or mixtures of any of these. Particularly preferred are tetrahydrofuran and alkyl-substituted tetrahydrofurans.

Other co-solvents or diluents may also be present in the reaction medium, such as one or more liquid paraffinic, cycloparaffinic and/or aromatic hydrocarbons. When utilized as co-solvents, preferred hydrocarbons are the liquid aromatic hydrocarbons such as benzene, toluene, xylenes, ethyl benzene, tetrahydronaphthalene, and the like. The mixed reaction media should contain by volume, a major amount (>50%) of the ether(s) and a minor amount (<50%) of the co-solvent(s).

The conditions for the reaction between the sodium diarylphosphide and/or potassium diarylphosphide and the alkyl-substituted cycloalkyl monochloride need not be severe. Temperatures in the range of about 40° and about 120° C. will normally suffice. A preferred range is from about 60° to about 100° C. The reaction is preferably performed at atmospheric pressure, although this is not essential. For example, if using an ether that has a boiling point below the reaction temperature selected for use, the reaction should be performed under super-atmospheric pressure sufficient to keep the ether in the liquid state. Likewise reduced pressure can be employed under suitable circumstances (e.g., use of a high boiling ether reaction medium, etc.). With a tetrahydrofuran reaction medium, reflux temperatures at atmospheric pressure is a desirable way to conduct the reaction. Proportions are not critical, but usually will be relatively close to equimolar, e.g., from about 0.8 to about 1.5 mols of the alkyl-substituted cycloalkyl monochloride per mol of the sodium and/or potassium diarylphosphide. The reaction should be conducted under a dry inert atmosphere.

In one embodiment of this invention, the sodium diarylphosphide and/or potassium diarylphosphide reactant is formed by cleaving a triaryl phosphite with sodium or potassium or a mixture or alloy of sodium and potassium in an ether reaction medium, and all or at least a portion of the resultant reaction mass and the partially sterically-hindered cycloalkyl chloride are mixed with each other and heated to cause formation of the cycloalkyldiarylphosphine. In this embodiment the two reactions are carried out sequentially preferably without replacing the ether used in the initial triarylphosphine cleavage reaction. However, additional solvent may be added in the second reaction and, alternatively, the solvent used in the initial reaction can be replaced in whole or in part by fresh solvent for the second reaction, if desired. The temperature used in the initial triaryl phosphine cleavage reaction is typically below 100° C., and the reaction often can be conducted at the reflux temperature of the lower boiling ether solvents used. Thus with tetrahydrofuran and sodium, the initial cleavage reaction is preferably conducted at or near reflux temperatures of about 65°–68° C. When potassium is used in the triaryl phosphine cleavage reaction, lower temperatures are usually employed, such as ambient room temperatures (e.g., 20°–25° C.).

Thus this invention further provides as one of its embodiments a two-stage process of forming a phosphine of the formula $R^1R^2R^3P$, wherein $R^1$ and $R^2$ are the same or different aryl groups, wherein $R^3$ is a mono- or polyalkyl-substituted cycloalkyl group having from 5 to 8 carbon atoms in the ring and having one of the ortho positions occupied by a linear or branched alkyl group having up to about 12 carbon atoms. This process comprises as the first stage reacting a triarylphosphine with metallic sodium or potassium, or a mixture or alloy thereof, in a liquid ether reaction medium in which the phosphine is soluble, in proportions such that a solution of (1) sodium diarylphosphide or potassium diarylphosphide, or a mixture thereof, and (2) sodium arylate or potassium arylate, or a mixture thereof, is formed. In the second stage at least a portion of the sodium diarylphosphide or potassium diarylphosphide, or mixture thereof, while in solution along with at least a portion of the sodium arylate or potassium arylate, or mixture thereof, is reacted with at least one mono- or polyalkyl-substituted 1-chlorocycloalkane having a single 5- to 8-membered ring which is substituted in one of the ortho positions relative to the chloro-substituted carbon atom by a linear or branched alkyl group having up to about 12 carbon atoms, to form a phosphine of the above formula $R^1R^2R^3P$.

As noted above, the ether reaction media used in the various embodiments of this invention are composed predominately of one or more ethers, that is, over 50% by volume is one or more ethers, and the balance, if any, is composed of one or more anhydrous liquid inert solvents such as ketones, esters, tertiary amines, and/or hydrocarbons. Of these, liquid hydrocarbons, especially saturated aliphatic hydrocarbons, saturated cycloaliphatic hydrocarbons, or aromatic hydrocarbons, or mixtures of such hydrocarbons are preferred. The most preferred co-solvents are the liquid aromatic hydrocarbons. As a general proposition, the higher the volume percentage of the ether(s) in the reaction medium, the better. Most preferably, therefore, substantially the entire reaction medium is composed of one or more ethers.

The following example is presented for the purposes of illustration and not limitation.

EXAMPLE

Preparation of Sodium DiphenylPhosphide

A solution of triphenylphosphine (20 grams, 0.0762 mol) in dry tetrahydrofuran (THF) (200 mL) is refluxed with freshly cut sodium (7 grams, 0.305 mol) under a nitrogen atmosphere for 15–20 hours. Sodium diphenylphosphide (NaDPP) is formed as a red solution which is decanted into the next reaction without further purification. In a reaction performed in this manner, the conversion to NaDPP was >97%.

Preparation of Neomenthyldiphenylphosphine

The NaDPP solution is placed in a flame dried flask. To this is added 15.96 grams (0.0914 mol) of menthyl chloride, and the mixture is heated to reflux. After 40 hours at refluxing temperature, the reaction mass is cooled to room temperature and quenched with water. The organic layer is separated and distilled to remove the solvents. The crude product is then dissolved in refluxing anhydrous methanol and cooled to obtain neomenthyl diphenyl phosphine (NMDPP) as white crystals. In a run performed in this manner without optimization, the recovered yield of NMDPP was 60%.

Each and every publication referred to in any portion of this specification is fully incorporated into this disclosure by reference as if fully set forth herein.

Formulas are used herein for the purpose of clarification and to facilitate discussion. In this connection, it is to be understood and appreciated that the formula given for the alkali metal diarylphosphides, although depicted in ionic format, should not be construed as requiring ionization of the alkali metal diarylphosphides at any time during the conduct of the process. Rather, it is intended that the alkali metal diarylphosphides, and indeed the other specified reactants, are in whatever chemical form they assume or acquire when brought together in the solvent or reaction media and when under the conditions specified for the particular reaction.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of forming a phosphine of the formula $R^1R^2R^3P$, which process comprises reacting an alkali metal diarylphosphide with an alkyl-substituted monochlorocycloalkane of the formula $R^3Cl$ in a liquid ether reaction medium in which said phosphide is soluble such that said phosphine is formed, wherein $R^1$ and $R^2$ are the same or different aryl groups, wherein $R^3$ is a mono- or polyalkyl-substituted cycloalkyl group having from 5 to 8 carbon atoms in the ring and where a linear or branched alkyl group of up to about 12 carbon atoms is substituted on one of the ortho positions of the ring, and wherein the alkali metal of the phosphide is a sodium or potassium atom.

2. A process according to claim 1 wherein said ether is a saturated hydrocarbyl ether, or a hydrocarbyl ether having at least one aromatic group in the molecule.

3. A process according to claim 1 wherein said ether is a dialkyl ether, a diaryl ether or a saturated cyclic monoether.

4. A process according to claim 1 wherein said ether is tetrahydrofuran.

5. A process according to claim 1 wherein $R^3$ is a mono- or polyalkyl-substituted cyclohexyl group having a branched alkyl group occupying one of the positions ortho to the ring carbon atom substituted by the chlorine atom.

6. A process according to claim 1 wherein $R^3$ is a dialkyl-substituted cyclohexyl group in which one of the alkyl groups is a branched alkyl group occupying one of the positions ortho to the ring carbon atom substituted by the chlorine atom.

7. A process according to claim 6 wherein said branched alkyl group is an isopropyl group and the other alkyl group is an unbranched alkyl group occupying a meta or para position relative to the ring carbon atom substituted by the chlorine atom.

8. A process according to claim 1 wherein said alkyl-substituted monochlorocycloalkane is menthyl chloride.

9. A process according to claim 1 wherein the alkali metal diarylphosphide is a sodium or potassium diphenylphosphide or a mixture of sodium and potassium diphenylphosphides in which the phenyl group is either unsubstituted or has up to 3 alkyl substituents having up to about 4 carbon atoms each.

10. A process according to claim 9 wherein the ether is a saturated cyclic monoether, and wherein $R^3$ is a dialkyl-substituted cyclohexyl group in which one of the alkyl groups is a branched alkyl group occupying one of the positions ortho to the ring carbon atom substituted by the chlorine atom.

11. A process according to claim 10 wherein the ether is tetrahydrofuran or an alkyl-substituted tetrahydrofuran.

12. A process according to claim 11 wherein the alkyl-substituted monochlorocycloalkane is menthyl chloride.

13. A process according to claim 12 wherein the alkali metal diarylphosphide is sodium diphenylphosphide or potassium diphenylphosphide, or a mixture thereof.

14. A process according to claim 13 wherein the alkali metal diarylphosphide is sodium diphenylphosphide and wherein the ether is tetrahydrofuran.

15. A process of forming a phosphine of the formula $R^1R^2R^3P$, wherein $R^1$ and $R^2$ are the same or different aryl groups, wherein $R^3$ is a mono- or polyalkyl-substituted cycloalkyl group having from 5 to 8 carbon atoms in the ring and having one of the ortho positions occupied by a linear or branched alkyl group having up to about 12 carbon atoms, which process comprises:

a) reacting a triarylphosphine with metallic sodium or potassium, or a mixture or alloy thereof, in a liquid ether reaction medium in which said phosphine is soluble, in proportions such that a solution of (1) sodium diarylphosphide or potassium diarylphosphide, or a mixture thereof, and (2) sodium arylate or potassium arylate, or a mixture thereof, is formed; and b) reacting (3) at least a portion of the sodium diarylphosphide or potassium diarylphosphide, or mixture thereof, while in solution along with at least a portion of the sodium arylate or potassium arylate, or mixture thereof, with (4) at least one mono- or polyalkyl-substituted 1-chlorocycloalkane having a single 5- to 8-membered ring which is substituted in one of the ortho positions relative to the chloro-substituted carbon atom by a linear or branched alkyl group having up to about 12 carbon atoms, to form a phosphine of said formula $R^1R^2R^3P$.

16. A process according to claim 15 wherein the reactions of a) and b) are carried out sequentially without replacing the ether used in a).

17. A process according to claim 15 wherein the aryl groups of the triaryl phosphine are the same, wherein the ether is a saturated cyclic monoether, and wherein said 1-chlorocycloalkane is a 1-chlorodialkylcyclohexane.

18. A process according to claim 15 wherein the ether is tetrahydrofuran or an alkyl-substituted tetrahydrofuran.

19. A process according to claim 15 wherein said 1-chlorocycloalkane is menthyl chloride.

20. A process according to claim 15 wherein the aryl groups of the triaryl phosphine are the same, wherein the ether is a saturated cyclic monoether, wherein the reactions of a) and b) are carried out sequentially without replacing the cyclic monoether, and wherein said 1-chlorocycloalkane is a 1-chlorodialkylcyclohexane.

21. A process according to claim 20 wherein the ether is tetrahydrofuran or an alkyl-substituted tetrahydrofuran.

22. A process according to claim 21 wherein said 1-chlorocycloalkane is menthyl chloride.

23. A process according to claim 22 wherein said triarylphosphine is triphenylphosphine.

24. A process according to claim 23 wherein the ether is tetrahydrofuran and the triphenylphosphine is reacted with sodium.

25. A process according to claim 23 wherein the ether is tetrahydrofuran and the triphenylphosphine is reacted with potassium.

26. A process according to claim 23 wherein the ether is tetrahydrofuran and the triphenylphosphine is reacted with a sodium-potassium alloy.

* * * * *